US010315029B2

(12) United States Patent
Tai

(10) Patent No.: US 10,315,029 B2
(45) Date of Patent: Jun. 11, 2019

(54) NON-INVASIVE METHOD TO TREAT UROLOGICAL AND GASTROINTESTINAL DISORDERS

(71) Applicant: University of Pittsburgh—Of the Commonwealth System of Higher Education, Pittsburgh, PA (US)

(72) Inventor: Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/848,143

(22) Filed: Dec. 20, 2017

(65) Prior Publication Data

US 2018/0133472 A1    May 17, 2018

Related U.S. Application Data

(63) Continuation of application No. 13/497,343, filed as application No. PCT/US2010/050883 on Sep. 30, 2010, now Pat. No. 9,878,154.

(60) Provisional application No. 61/247,659, filed on Oct. 1, 2009.

(51) Int. Cl.
*A61N 1/36* (2006.01)

(52) U.S. Cl.
CPC ..... *A61N 1/36007* (2013.01); *A61N 1/36014* (2013.01)

(58) Field of Classification Search
CPC ............ A61N 1/36014; A61N 1/36007; A61N 1/36071; A61N 1/36107; A61N 1/321; A61H 39/00; A61H 39/002; A61H 2205/125; Y10S 128/907

See application file for complete search history.

(56) References Cited

U.S. PATENT DOCUMENTS

| 4,454,883 | A  | 6/1984  | Fellus            |
|-----------|----|---------|-------------------|
| 6,701,185 | B2 | 3/2004  | Burnett et al.    |
| 7,047,078 | B2 | 5/2006  | Boggs, II et al.  |
| 8,435,166 | B2 | 5/2013  | Burnett et al.    |
| 2004/0044384 | A1 | 3/2004 | Leber et al.     |
| 2004/0254624 | A1 | 12/2004 | Johnson         |
| 2005/0143783 | A1 | 6/2005 | Boveja et al.    |
| 2008/0033510 | A1 | 2/2008 | Herregraven et al. |
| 2008/0306325 | A1 | 12/2008 | Burnett et al.   |
| 2009/0036945 | A1 | 2/2009 | Chancellor et al. |

(Continued)

OTHER PUBLICATIONS

Andersson, Karl-Erik et al., "Pharmacology of the Lower Urinary Tract: Basis for Current and Future Treatments of Urinary Incontinence", Pharmacological Review, 2004, pp. 581-631, vol. 56, No. 4.

(Continued)

*Primary Examiner* — Tammie K Marlen
(74) *Attorney, Agent, or Firm* — The Webb Law Firm

(57) ABSTRACT

Provided herein are methods and devices useful for inhibiting or treating urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder by non-invasive transcutaneous electrical stimulation of the foot.

20 Claims, 10 Drawing Sheets

(56) References Cited

U.S. PATENT DOCUMENTS

| | | |
|---|---|---|
| 2010/0145413 A1 | 6/2010 | Brogan et al. |
| 2010/0204538 A1 | 8/2010 | Burnett et al. |
| 2011/0270140 A1 | 11/2011 | Israeli |
| 2012/0101326 A1 | 4/2012 | Simon et al. |

OTHER PUBLICATIONS

De Groat, William C. et al., "Developmental and injury induced plasticity in the micturition reflex pathway", Behavioural Brain Research, 1998, pp. 127-140, vol. 92.

Godec, C., "Electrical stimulation for incontinence. Technique, selection and results.", Urology, 1975, pp. 338-397, vol. 7, Issue 4.

Lindstrom, Sivert et al., "The Neurophysiological Basis of Bladder Inhibition in Response to Intravaginal Electrical Stimulation", The Journal of Urology, 1983, pp. 405-410, vol. 129, Issue 2.

McGuire, EJ, "Treatment of motor and sensory detrusor instability by electrical stimulation", The Journal of Urology, 1983, pp. 78-79, vol. 129, Issue 1.

McPherson, Angus, "The Effects of Somatic Stimuli on the Bladder in the CAT", J. Physiol., 1966, pp. 185-196, vol. 185.

Nakib, Nissrine et al., "Neuromodulation versus neurotoxin for the treatment of refractory detrusor overactivity: for neuromodulation", Nature Clinical Practice Urology, 2008, pp. 118-119, vol. 5, No. 3.

Peters, Kenneth M. et al., "Sacral Versus Pudendal Nerve Stimulation for Voiding Dysfunction: A Prospective, Single-Blinded, Randomized, Crossover Trial", Neurology and Urodynamics, 2005, pp. 643-647, vol. 24.

Peters, Kenneth M. et al., Randomized Trial of Percutaneous Tibial Nerve Stimulation Versus Extended-Release Tolterodine: Results From the Overactive Bladder Innovative Therapy Trial, The Journal of Urology, 2009, pp. 1055-1061, vol. 182.

Peters, Kenneth M. et al., "A prospective, single-blind, randomized crossover trial of sacral vs pudendal nerve stimulation for interstitial cystitis", Journal Compilation, 2007, pp. 835-839, vol. 100.

Queralto, M. et al., "Preliminary results of peripheral transcutaneous neuromodulation in the treatment of idiopathic fecal incontinence", Int J Colorectal Dis, 2006, pp. 670-672, vol. 21.

Sato, A. et al., "Reflex bladder activity induced by electrical stim", Journal of the Autonomic Nervous System, 1980, pp. 229-241, vol. 1, Issue 3.

Shen, B. et al., "Bladder activity modulated by transcutaneous pudendal nerve stimulation", Neuroscience, 2008, Online, pp. 1-2.

Sutherland, Suzette E. et al., "Sacral Nerve Stimulation for Voiding Dysfunction: One Institution's 11-Year Experience", Neurology and Urodynamics, 2006, pp. 19-28, vol. 26.

Tai, Changfeng et al., "Inhibitory and excitatory perigenital-to-bladder spinal reflexes in the cat", Am J Physiol Renal Physiol, 2007, pp. F591-F602, vol. 294.

Tai, Changfeng et al., "Pudendal-to-bladder reflex in chronic spinal-cord injured cats", Experimental Neurology, 2006, pp. 225-234, vol. 197.

Van Balken, Michael R., "Percutaneous tibial nerve stimulation: the Urgent PC.sup.[R] device", Expert Review of Medical Devices, 2007, p. 693, vol. 4.5.

Van Der Pal, Floor et al., "Percutaneous tibial nerve stimulation in the treatment of refractory overactive bladder syndrome: is maintenance treatment necessary?", BJU International, 2006, pp. 547-550, vol. 97.

Vitton, Veronique et al., "Transcutaneous Posterior Tibial Nerve Stimulation for Fecal Incontinence in Inflammatory Bowel Disease Patients: A Therapeutic Option?", Inflamm Bowel Dis, 2009, pp. 402-405, vol. 15, No. 3.

Walter, James S. et al., "Inhibiting the Hyperreflexic Bladder With Electrical Stimulation in a Spinal Animal Mode", Neurology and Urodynamics, 1993, pp. 241-253, vol. 12.

Wang, Jicheng et al., "Bladder Inhibition or Excitation by Electrical Perianal Stimulation in the Chronic SCI Cat", BJU Int., 2009, pp. 1-13, vol. 103(4).

Wheeler, John S., Jr., et al., "Bladder Inhibition by Penile Nerve Stimulation in Spinal Cord Injury Patients", The Journal of Urology, 1982, pp. 100-103, vol. 147.

A. Electrodes 1-2, Hind Foot

20 Hz, 10 V    5 Hz, 10 V = 1T

B. Electrodes 1-3, Hind Foot 10 minutes

20 Hz, 11 V    5 Hz, 11 V = 2T

C. Electrodes 2-3, Hind Foot 40 cmH$_2$O    150 sec

5 Hz, 12 V = 1.5T    20 Hz, 12 V

D. Electrodes 1-2, Front Foot

5 Hz, 15 V = 2.5T    20 Hz, 15 V

A. CMG

B. Isovolumetric

NON-INVASIVE METHOD TO TREAT UROLOGICAL AND GASTROINTESTINAL DISORDERS

CROSS REFERENCE TO RELATED APPLICATIONS

This application is a continuation of U.S. patent application Ser. No. 13/497,343, filed Sep. 10, 2012, now issued as U.S. Pat. No. 9,878,154, which is a National Stage of International Patent Application Number PCT/US2010/050883, filed Sep. 30, 2010, which claims the benefit under 35 U.S.C. § 119(e) to U.S. Provisional Patent Application No. 61/247,659, filed Oct. 1, 2009, each of which is incorporated herein by reference in its entirety.

STATEMENT REGARDING FEDERALLY SPONSORED RESEARCH OR DEVELOPMENT

This invention was made with government support under Grant Nos. DK-068566 and DK-077783 awarded by the National Institutes of Health. The government has certain rights in the invention.

BACKGROUND

It is well-known that electrical stimulation of somatic afferent pathways in the pudendal nerve, posterior tibial nerve, or sacral spinal roots can inhibit bladder activity in both humans and animals, and is clinically effective in treating overactive bladder symptoms. Stimulation of the sacral S3 spinal root is currently a FDA approved therapy for the lower urinary tract disorders including bladder overactivity, urgency, frequency, incontinence, and urinary retention. Although the mechanisms underlying neuromodulation are uncertain, this type of therapy has become popular because lower urinary tract dysfunctions in some patients are difficult to manage with medication.

However, sacral and pudendal neuromodulation requires surgery to implant a stimulator (e.g., InterStim®, Medtronic Inc.) and electrodes. Meanwhile, the standard treatment using tibial nerve neuromodulation involves 30 min stimulation once per week for 12 consecutive weeks through a percutaneously inserted needle electrode cephalad to the medial malleolus (Urgent PC® stimulator, Uroplasty Inc.). It requires skilled medical staff to insert the needle electrode close to the nerve during each clinical visit. If the initial 12 week treatment is effective, a maintenance treatment (once every 2-3 weeks) is usually required. Thus, current neuromodulation treatments are effective to suppress bladder overactivity, but they require surgery or repeated clinical visits that are expensive and inconvenient. A non-invasive neuromodulation method to treat overactive bladder could significantly increase the acceptance of neuromodulation treatment by more patients and reduce the high medical cost of the treatment.

Several non-invasive neuromodulation approaches have been investigated previously in an attempt to treat bladder overactivity, including intra-vaginal (Lindstrom S, Fall M, Carlsson C A, Erlandson B E. The neurophysiological basis of bladder inhibition in response to intravaginal electrical stimulation. J Urol 1983; 129: 405-410) or intra-anal (Godec C, Cass A S, Ayala G F. Bladder inhibition with functional electrical stimulation. Urol 1975; 6:663-666) simulation using ring electrodes located on a vaginal/anal plug, dorsal penile/clitoral nerve stimulation using transcutaneous electrical stimulation applied to the penis, or the perigenital/perianal skin area (Tai C, Shen B, Wang J, Chancellor M B, Roppolo J R, de Groat W C: Inhibitory and excitatory perigenital-to-bladder spinal reflexes in the cat. Am J Physiol Renal Physiol 2008; 294:F591-F602; Wheeler J S, Walter J S, Zaszczurynski P J. Bladder inhibition by penile nerve stimulation in spinal cord injury patients. J Urol 1992; 147:100-103; Walter J S, Wheeler J S, Robinson C J, Wurster R D. Inhibiting the hyperreflexic bladder with electrical stimulation in a spinal animal model. Neurourol Urodyn 1993; 12:241-253; and Wang J, Liu H, Shen B, Roppolo J R, de Groat W C, Tai C: Bladder inhibition or excitation by electrical perianal stimulation in a cat model of chronic spinal cord injury. BJU Int 2009; 103:530-536). However, these approaches targeted very inconvenient locations causing discomfort and difficulty in maintaining the electrodes in place for an extended time period.

SUMMARY

The methods and devices described herein are useful for stimulating a physiological response and for inhibiting or treating conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder and female sexual arousal disorder.

The methods and devices are superior to prior methods because they do not involve invasive activities, such as electrode implantation, for instance, as is currently used for urinary incontinence, and do not require precise placement of the electrodes. The methods involve electrical stimulation applied to the skin of the foot of a patient, unexpectedly being able to inhibit bladder contractions in a non-invasive manner that is easily implemented by patients and which is amenable to use of garment electrodes, such as sock electrodes, greatly enhancing patient independence and reducing costs of such procedures.

A method of stimulating a physiological response in a subject is provided. The method comprises applying transcutaneous electrical pulses ranging from 1 Hz to 500 Hz and from 1V to 50V to the patient's foot (one or both feet of the patient) effective to stimulate a physiological response selected from the group consisting of inhibiting or treating in the patient one or more of: bladder contractions; rectum contractions; bulbospongiosus and ischiocavernosus muscle contractions; urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder. In one embodiment, the method comprises inhibiting bladder contractions in a patient by applying transcutaneous electrical pulses ranging from 1 Hz to 500 Hz, 0.1 ms to 3 ms and from 1V to 50V to the patient's foot effective to inhibit bladder contractions in the patient. The electrical pulses are applied in certain embodiments by one or more electrodes on skin of the dorsal side of the patient's foot about one or more metatarsal bones and one or more opposite electrodes (an "opposite electrode" is one that is oppositely charged in relation to another, e.g. a cathode is an opposite electrode to an anode) on skin of the plantar side of the patient's foot about one or more metatarsal bones. In another embodiment, the electrical pulses are applied by one or more electrodes on skin of the dorsal side of the patient's foot about one or more metatarsal bones and one or more opposite electrodes on skin of the dorsal side of the patient's foot about one or both of the talus, cuboid, intermediate cuneiform, lateral cuneiform or navicular bones. In yet another embodiment, the electrical pulses are applied by one or more electrodes on skin of the plantar side of the patient's foot about the tarsal bones and one or more opposite electrodes on skin of the plantar side of the patient's foot about the calcaneous bones. The electrode may be any useful electrode configuration for stimulation the foot, for example a garment electrode, such as a sock electrode.

The electrical pulses may be any waveform, or mixture thereof, effective to stimulate the desired response. In one embodiment, the pulses are biphasic, symmetrical and/or rectangular and preferably the biphasic pulses are charge-balanced. The pulses can be applied for any effective time period or pattern. For example, in one embodiment, the pulses are applied in two or more stimulation intervals of from 0.5 to 200 seconds with a rest period of no electrical stimulation able to cause bladder or rectal inhibition during stimulation intervals. In another embodiment, the pulses are applied at a voltage less than an intensity threshold to induce toe movement (T) in a patient. In certain embodiments, the pulse frequency ranges from 1 to 50 Hz, 5 to 20 Hz or is approximately 5 Hz. In certain embodiments, the voltage ranges from 3V to 12V and may range from 0.5T to 2T, where T is the toe-twitch threshold of a patient. In certain embodiments, the pulse duration ranges from 0.1 to 3 ms, 0.2 to 1 ms or is approximately 1 ms.

Also provided is a device for use in stimulating a physiological response in a patient for inhibiting or treating in the patient one or more of: bladder contractions; rectum contractions; bulbospongiosus and ischiocavernosus muscle contractions; urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder. The device comprises an electrical pulse generator, an electrode assembly comprising two or more skin surface electrodes configured to position electrodes on a patient's foot such that the electrodes can be used to stimulate the physical response and leads (e.g., wire leads) connecting the electrodes to the pulse generator, wherein the pulse generator is configured to produce electrical pulses in the range of from 1 Hz to 500 Hz and from 1V to 50V to stimulate the physiological response in the patient. In one embodiment, the electrodes are in a garment electrode for the foot, such as a sock electrode. In certain embodiments, the pulse frequency ranges from 1 to 50 Hz, 5 to 20 Hz or is approximately 5 Hz. In certain embodiments, the voltage ranges from 3V to 12V and may range from 0.5T to 2T, where T is the toe-twitch threshold of a patient. In certain embodiments, the pulse duration ranges from 0.1 to 3 ms, 0.2 to 1 ms or is approximately 1 ms.

According to certain embodiments, the pulse generator is attached to a garment electrode for a foot comprising the electrodes and comprises an antenna and the pulse generator is controllable by an external transmitter that transmits a signal that is received by the antenna of the pulse generator and data can be transmitted from the pulse generator to an external receiver. In one embodiment, the external receiver is contained in a device comprising the transmitter. In certain embodiments, the external transmitter transmits an identification signal to the pulse generator, the pulse generator requiring an appropriate identification signal from the transmitter to control output of the pulse generator. In another embodiment, one of the pulse generator and the transmitter comprises an RFID tag and the other of the pulse generator and the transmitter comprises an RFID reader and verification of the identity of the pulse generator and transmitter by RFID is required to control output of the pulse generator. In yet another embodiment, signals from the transmitter are encrypted and can only be decrypted by a matching pulse generator. As a safety measure, in one embodiment of the device, one of the pulse generator and the transmitter require identification of the other before the transmitter can control output of the pulse generator

DETAILED DESCRIPTION

Figure 1:
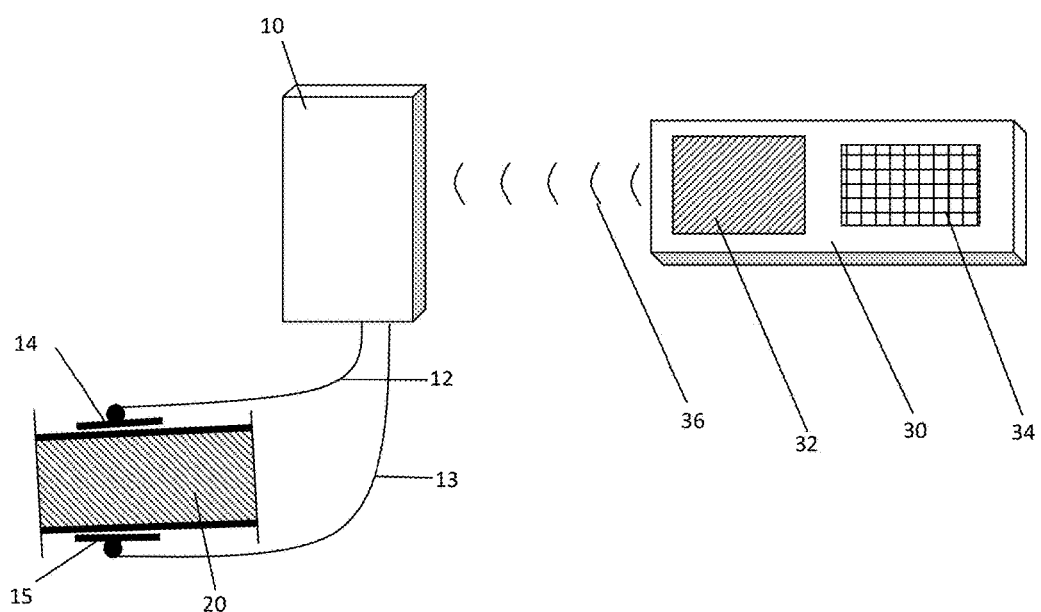
FIG. 1 is a schematic diagram of one non-limiting embodiment of a device useful in implementing methods described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

The ranges provided herein for e.g., electric pulse frequencies are based on experimentation on cats. Nevertheless, the frequencies necessary to elicit a desired response in humans is very similar. As illustrated in U.S. Pat. No. 7,047,078, stimulation of the pudendal nerve in human subjects produce similar results as compared to the results in cats. As such, frequency ranges applicable to cats are considered to be effective in humans.

Stimulus effective to inhibit bladder contractions is expected to also affect gastrointestinal and sexual conditions including: urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder and female sexual arousal disorder. For example, sacral neuromodulation (e.g., InterStim, Medtronic Inc) can treat both overactive bladder and urinary retention. In another example, transcutaneous stimulation of the tibial nerve approximately 10 cm above the ankle has shown some limited potential in alleviating urinary and fecal incontinence (see e.g., Queralto et al. Preliminary results of peripheral transcutaneous neuromodulation in the treatment of idiopathic fecal incontinence Int J Colorectal Dis (2006) 21: 670-672 and Vitton et al. Transcutaneous Posterior Tibial Nerve Stimulation for Fecal Incontinence in Inflammatory Bowel Disease Patients: A Therapeutic Option? Inflamm Bowel Dis 2009; 15:402-405), though these methods are sub-optimal because they require precise placement of the electrode over the tibial nerve and are not believed to stimulate substantially, if at all, any nerves in addition to the tibial nerve. It is believed that sacral neuromodulation modulates the central nervous system (CNS) by stimulating the sacral root and sending neural activity into the CNS. This neuromodulation input can make the CNS balance to one way the other, that is, if it is overactive bladder it will make the CNS to be more inhibitory to the bladder activity, but if it is urinary retention, then the neuromodulation will make the CNS more excitatory to the bladder. The underlying mechanisms are very complex and not fully understand yet.

The foot stimulation methods described herein are another type of neuromodulation. They send modulatory neural signal from the foot nerves to the CNS. The Examples below show that this foot neuromodulation can modulate the CNS to inhibit the bladder. This does not mean that foot neuromodulation can only induce inhibitory effect. When the pathological condition is the opposite (for example, urinary retention), the foot neuromodulation should be able to modulate the CNS to facilite bladder contraction or facilite voiding. In summary, foot stimulation is another type of neuromodulation that can induce either inhibitory or excitatory effect depending on the state of the CNS (that is, exciting or inhibiting an organ). Now, we know that stimulation of the foot nerve (somatic nerve) can modulate the bladder (autonomic organ), therefore it is logical and reasonable to conclude it will also modulate other autonomic organs (e.g., defecation or sexual functions).

It should also be recognized that the optimal stimulation parameters to elicit a desired effect may vary to some degree from subject-to-subject, depending on a number of factors. Optimal frequencies to elicit the desired goals can be adjusted from person-to-person. A "patient" may be human or animal and unless specified otherwise embraces a specific patient, a class of patients or any human or animal in a generic sense. Thus, a structure configured to, or adapted to, a patient's foot includes structures configured to a specific patient and/or a group of patients.

According to one non-limiting embodiment, method of inhibiting or controlling one or more of bladder contractions; rectum contractions; bulbospongiosus and ischiocavernosus muscle contractions; urination; defecation; ejaculation; and pelvic pain of the bladder, urethra, prostate, anus or rectum in a patient is provided. The methods are useful in inhibiting or treating urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder and female sexual arousal disorder. In one embodiment the method is directed to a method of inhibiting bladder contractions, bowel and/or rectum contractions, and therefore urination and/or defecation in a patient. The method comprises inhibiting one or more of bladder contractions, bowel and/or rectum contractions, and therefore urination and/or defecation in the patient by applying an electrical signal to the foot of a patient.

Either one or both (left and right) of the feet can be stimulated concurrently, alternately or in any useful sequence to achieve the desired results. Most generally, electrodes are positioned on the foot at a position such that when electric pulses of sufficient voltage, duration and frequency to inhibit bladder or GI contractions is applied, the stimulus can be used to treat urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder. Certain parameters are discussed below which are expected to elicit such a response in a patient. Nevertheless, the following ranges and embodiments are exemplary and any variation from the stated ranges capable of eliciting the desired response is considered to be within the scope of the methods described herein. As such any methods or devices described herein are expected to be useful for controlling or treating urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder and female sexual arousal disorder or any other disease or condition that would benefit from relief of contractions in the lower pelvis (e.g., contractions of the bladder or rectum).

Any positioning of an electrode pair on the foot (to include the ankle joint, that is, at or below the ankle (talocrural) joint of a patient) that is useful in inhibiting bladder, rectal or ejaculatory contractions/activity are considered within the scope of the present methods and devices and alteration of the specific positioning described below that are useful in the described methods are considered to be within the scope of the described methods. The following is a description of three exemplary positioning for the electrodes: 1) two electrodes attached on the bottom of the foot, between one or more metatarsal bones and calcaneus bones; 2) two electrodes attached on top of the foot: between one or both of the talus, cuboid, intermediate cuneiform, lateral cuneiform or navicular bones and one or more metatarsal bones; or 3) two electrodes attached one on top and another on the bottom of the foot: across the metatarsal bones.

These configurations do not necessarily stimulate one particular nerve because the electrical pulses pass through the foot and are not targeted to specific nerves. Although there are other nerves in the foot, without any attempt to be bound by this theory, the methods described herein stimulate the peroneal and tibial nerves and/or branches thereof, such as the medial plantar and lateral plantar branches of the tibial nerve. As used herein, the electrodes are said to be on skin "about" a specific bone (e.g. about one or more metatarsal bones) when they are placed, located (etc.) on skin that covers or partly covers the specified bone—that is, the specified bone lies partially or wholly underneath the skin said to be "about" the specified bone. Skin "about" a specified bone can overlap the specified bone and another bone.

The electrodes can be any skin surface electrode, such as, without limitation, self-adhesive skin surface electrodes. For example, a large variety of useful electrodes and electrode configurations are well-known in the medical arts and are available commercially for use in, e.g., TENS (Transcutaneous Electrical Nerve Stimulation), NMES (Neuromuscular Electrical Stimulation), patterned Electrical Neuromuscular Stimulation (PENS), and Interferential Current (IFC), methods and devices. Alternately, the electrodes can be built into a sock, shoe, bandage, wrap or other foot covering so that the described methods can be performed discretely, e.g., at work. For instance electrode socks are available for diabetic foot care, though the electrodes are not necessarily configured to be useful for the purposes described herein. Commercial examples of sock devices (electrode sock) include the ELECRO-MESH™ garments (Prizm Medical, Inc. of Oakwood Ga.). United States Patent Publication No. 20040254624 describes various garment electrode devices. So long as the electrode is capable of delivering an electrical current to the skin of a patient when placed on a patient's foot at a position useful in the methods described herein, it is considered to be useful in the methods and devices described herein.

Figure 2A:
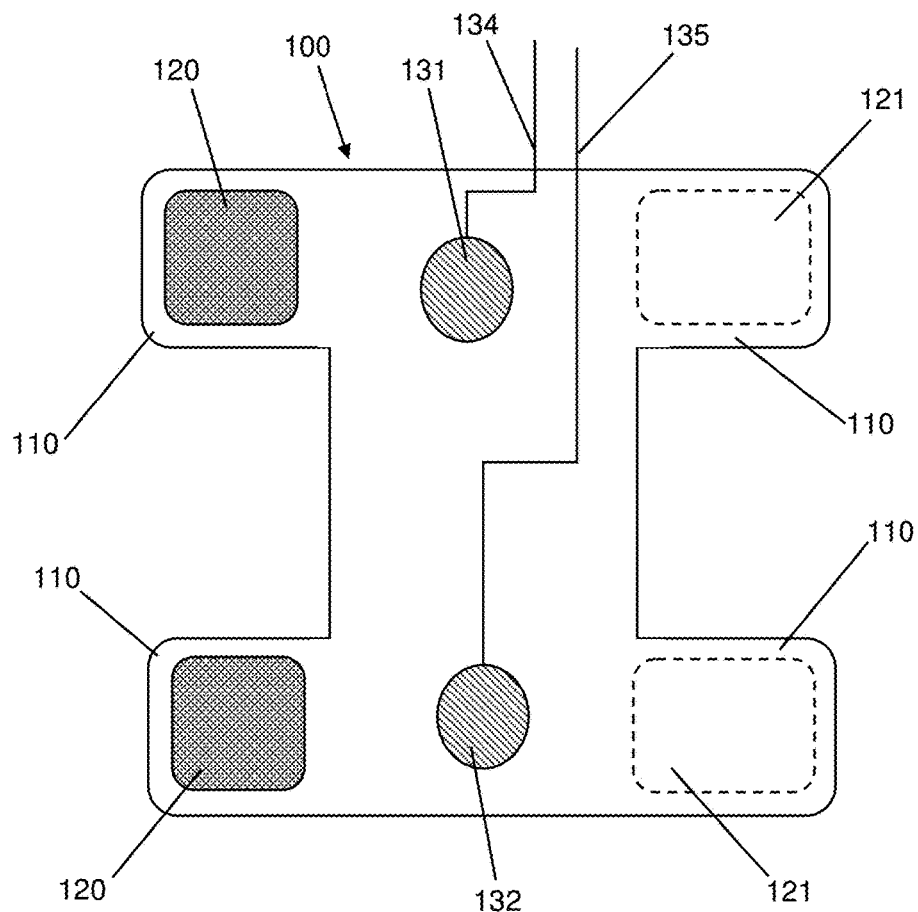
FIGS. 2A and 2B show schematically two embodiments of garment electrode assemblies useful in a device such as the device depicted in FIG. 1
Figure 2B:
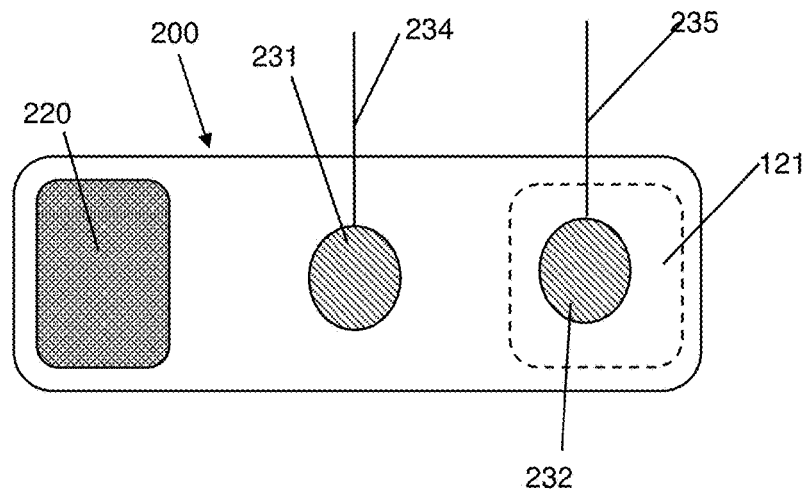

Structures comprising electrodes, such as shoes (sneakers, sandals etc.), socks, wraps, bandages (including ankle/foot supports or brace products comprising, e.g., neoprene), etc. that are useful in the methods and devices described herein and can be formed in any configuration or structure that facilitates positioning and contact of the electrodes with the foot. A "garment electrode" is an electrode assembly configured to replicate a piece of clothing, such as a sock, shoe, wrap, support or bandage, comprising electrodes configured to contact a patient's skin, e.g., in a position useful for inhibiting bladder contractions in the methods described herein. In one embodiment, a garment electrode is a wrap with Velcro (hook and loop) closures that fits around a patient's foot. FIGS. 2A and 2B, described below, depicts schematically non-limiting examples of such structures.

Description of all possible effective structures is impossible. As such, an electrode assembly "configured to" position electrodes on a patient's foot for inhibiting bladder contractions, GI contractions and/or ejaculation, or "configured for" use in inhibiting bladder contractions, GI contractions and/or ejaculation in a patient, is intended to embrace those electrode assemblies that are useful any method or device described herein. As indicated above, the structure may be designed to fit a specific patient, group of patients (e.g. a women's size 8 (US) shoe, or a men's size 10-13 (US) shoe) or all or substantially all patients (e.g., one size fits all).

The electrical signal comprises administering electrical pulses effective to inhibit bladder and/or bowel contractions or ejaculation. This is thought to produce a storage stage, similar to the typical storage stage of the normal micturition or defecation processes. The inhibitory or blocking electrical signal is thought to inhibit contraction of one or both of the external urethral sphincter and the anal sphincter of the subject. As will be recognized by a person of skill in the art, characteristics of electrical pulse, including, without limitation, amplitude (pulse strength, referring to the magnitude or size of a signal voltage or current), voltage, amperage, duration, frequency, polarity, phase, relative timing and symmetry of positive and negative pulses in biphasic stimulation, and/or wave shape (e.g., square, sine, triangle, sawtooth, or variations or combinations thereof) may be varied in order to optimize results in any particular subject or class of subjects. Subjects may be classified by species, disease/condition, sex, or any other factor that can be generalized to a group. Stated ranges are intended to include all values and ranges within the stated ranges. So long as other characteristics of the electrical signals (e.g., without limitation, amplitude, voltage, amperage, duration, polarity, phase, relative timing and symmetry of positive and negative pulses in biphasic stimulation, and/or wave shape) are within useful ranges, modulation of the pulse frequency will achieve a desired result. Useful values for those other characteristics are well-known in art and/or can be readily established by routine experimentation, for instance by the ability to prevent voiding by methods described herein.

One characteristic of the electrical signals used to produce a desired response, as described above, is pulse frequency. Although effective ranges (e.g., frequencies able to produce a stated effect) may vary from subject-to-subject, and the controlling factor is achieving a desired outcome, certain, non-limiting exemplary ranges may be as follows. For inhibiting bladder, bowel or sexual gland/muscle contractions, those frequencies may range from approximately 1 Hz (Hertz, or pulses per second) to approximately 500 Hz, though in practice, the range may be more typically 1-50 Hz, the range typically used for human nerve stimulation. Data below shows a range of at least from 5-20 Hz, with 5 Hz pulses being preferred in some instances. Useful pulse durations typically range from 0.1 to 3.0 ms (milliseconds), for example 0.2-1.0 ms or 1 ms pulses.

Another characteristic of the pulses are the Voltage. Nerve stimulation can be achieved in a typical range of from 1-50V, for example 3-15V as shown in the Examples below, with a range of from 1 to 15-20V being preferred in many instances. The typical voltage for foot stimulation may be from 0.25 to 5 times the toe twitch motility threshold (0.25T-5T, where the pulses case toe twitching). In some instances bladder, bowel, ejaculation and/or pelvic pain inhibition may be achieved at voltages less than 1.0T, such that the electrical stimulation causes no foot twitch, but has the desired inhibitory effect (see, e.g., FIG. 5A, where 0.5T pulses are shown to be able to inhibit bladder contractions).

As indicated above, the waveform of the pulses may vary, so long as the desired inhibitory effect is realized. One skilled in the art will appreciate that other types of electrical stimulation may also used in accordance with the present invention. Monophasic or biphasic stimuli, or a mixture thereof may be used. Biphasic stimulus may be preferred as there is less chance of tissue damage over the long-term. Damage to nerves by the application of an electrical current may be minimized, as is known in the art, by application of biphasic pulses or biphasic waveforms to the nerve(s), as opposed to a monophasic pulses or waveforms that can damage nerves in some instances of long-term use. "Biphasic current," "biphasic pulses" or "biphasic waveforms" refer to two or more pulses that are of opposite polarity that typically are of equal or substantially equal net charge (hence, biphasic and charge balanced) and may be symmetrical asymmetrical or substantially symmetrical. This is accomplished, for example, by applying through an electrode one or more positive pulses, followed by one or more negative pulses, typically of the same amplitude and duration as the positive pulses, or vice versa, such that the net charge applied to the target of the electrode is zero or approximately zero. The opposite polarity pulses may have different amplitudes, profiles or durations, so long as the net applied charge by the biphasic pulse pair (the combination of the positive and negative pulses) is approximately zero.

The waveform may be of any useful shape, including without limitation: sine, square, rectangular, triangle sawtooth, rectilinear, pulse, exponential, truncated exponential, damped sinusoidal. The pulses may increase or decrease over the stimulus period. The pulses may be applied continuously or intermittently as needed. As indicated below, stimulation of the foot at certain voltages for certain time periods elicits post-stimulus inhibition of bladder contractions. Therefore, the stimulus may be applied for short intervals (e.g. 1-10 minutes) to achieve longer-lasting relief, in terms of hour or days. The stimulus may be applied intermittently (that is, the pulses are turned on and off alternately during a stimulus interval for any time period) during continuous or interval stimulus protocols. For example, the stimulus may be applied for 5 seconds on and 5 seconds off over an interval of, for example, 1-10 minutes or longer. Other non-limiting examples of intermittent application of pulses may be 1-90 seconds on and 1-90 seconds off over a 1-30 minute time period. So long as other pulse parameters are within acceptable limits, the inhibition is temporary and does not damage the involved nerves.

In another embodiment, a device or system for use in inhibiting in a patient one or more of: bladder contractions; rectum contractions; bulbospongiosus and ischiocavernosus muscle contractions; urination; defecation; ejaculation; and pelvic pain of the bladder, urethra, prostate, anus or rectum is provided. The system comprises a pulse generator unit configured to produce electric pulses able to inhibit contraction of the bladder or bowel or to inhibit ejaculation. As indicated above, the frequency ranges from 1 Hz to 500 Hz, such as 1-50 Hz, 5-20 Hz, or 5 Hz. Voltage may range from 1-50V, such as from 1-20V or from 3-15V. The device or system may be set to produce pulses continuously or intermittently as described above, and can be controllable by the patient. The device also comprises an electrode assembly configured to or adapted for placement of two or more electrodes on the foot of a patient in a position suitable for producing the desired stimulation in the methods described herein.

In practice, the pulse generator may be programmable, programmed, non-programmable, or otherwise adapted to or configured to produce pulses within the ranges described herein as being useful for the stated purpose. For example, a commercial multi-purpose electrical stimulator for use in, e.g., TENS or NEMS, may be adjusted to the parameters useful in the methods described herein. In one non-limiting example, the device is non-programmable, having a prefixed output for voltage, pulse frequency, pulse length, and/or stimulus pattern/interval that cannot be changed. For instance, in one embodiment, the device produces 1 ms pulses at 5 Hz and 11V for 150 seconds whenever the device is activated either by the patient or another, or at specific intervals, for example hourly. Other settings may be any useful stimulation parameters within the ranges described above as being useful in the methods described herein. In another example, the device has two or more pre-fixed settings that cannot be changed, so that a patient or health care provider can choose the most effective stimulation parameter for the patient or for the patient's particular circumstances (e.g., in a meeting versus before bed). The frequency might be adjustable or achieved in any manner within any range described herein. Programmable or fixed-output electrical pulse generators are common and configuration to the stimulation parameters described herein is well within the abilities of those of ordinary skill in the art.

The pulse generation unit may comprise a first wireless communication system for receiving control instructions from a wireless controller; and a wireless controller, comprising an input, an optional display and a second wireless communication system configured to send control instructions to the pulse generator. In one embodiment, the electric pulses are biphasic. The first wireless communication system may also transmit status information for the pulse generator to the wireless controller. Further description of one embodiment of such a system is described in reference to FIG. 1. The phrases "configured to" and "adapted to" and like terms or phrases refer to the manufacture, production, modification, etc. of a device or system to produce a desired function. In the context of the devices or systems described herein, a device or system "adapted to" or "configured to" produce a desired output is a device programmed of otherwise manufactured, produced, modified, etc. in any manner to produce the stated effect.

FIG. 1 depicts schematically one non-limiting embodiment of a two-channel system for stimulating foot nerves according to the methods described herein. Pulse generator 10 is depicted as having two output channels. Wire leads 12 and 13 are attached to electrodes 14 and 15, which are placed across the metatarsal region of a foot 20. Electrode 15 is shown on the plantar side of the foot while electrode 14 is shown on the plantar side of the foot. Output parameters of the pulse generator 10 can be controlled via a wired interface, but also may be controlled by wireless transmission, which can be carried any suitable wireless protocol, such as radio frequency, IEEE 802.11a/b/g/n, Bluetooth, etc. Thus, an external controller 30 is depicted for communicating with the pulse generator 10. External controller 30 is depicted as having a display 32, such as an LCD, LED or OLED display, and a keypad 34 for entering data into the external controller 30. External controller is depicted as sending a wireless transmission 36 to pulse generator 10, though in another embodiment, data can be transferred both to the pulse generator 10 from the external communicator 30 and vice-versa, to permit monitoring of one or more parameters of pulse generator 10, including, without limitation, output signal characteristics (e.g., frequency, amplitude, etc. as outlined above) and battery strength. Likewise wireless transmission 36 can be replaced by a wire or other conductor. Activity of pulse generator 10 and external controller 30 typically is microprocessor controlled and software/firmware installed onto the pulse generator 10 and external controller 30 hardware may be used to implement the described tasks, and to provide, for example and without limitation, a GUI (graphical user interface) for the display 32, which facilitates use of the system. Both pulse generator 10 and external controller 30 may comprise any suitable electrical and electronic components to implement the pulse, communication, feedback, adjustment, etc. activities, including, microprocessors, memory (e.g., RAM, ROM. Flash memory, etc.), connectors, batteries, power transformers, amplifiers, software (including, for example and without limitation: firmware, operating systems, utilities, processes, routines), etc. A person of skill in the electronic arts will be able to implement such a system using readily-available electronics parts and ordinary programming skills. Proprietary chips, chipsets, etc. may be designed and manufactures to implement the devices described herein.

External controller 30 may be a proprietary device that is specifically designed for the task, or a non-proprietary device, such as a commercial TENS controller, smart phone or a portable computer. Pulse generator 10 may comprise any number of channels, so long as the number of channels needed to implement a desired method is provided. In one variation of the embodiment depicted in FIG. 1, one or both of wire leads 12 and 13 are split into two or more wire leads, each of which are terminated in a separate electrode, so that more than one region of the foot is stimulated.

One potential difficulty with use of wireless devices is one of identity. A controller should only be able to control one pulse generator to prevent accidental stimulation of unintended subjects, or even intentional stimulation. In its simplest form, the transmission range of the devices can also be limited to prevent transmission over distances more than a few feet, thereby limiting the chances of unintended stimulation (crosstalk). Also, any number of identity verification mechanisms may be utilized to prevent crosstalk. In one embodiment, different transmission wavelengths may be used for different devices, thus lowering the likelihood of crosstalk. In another embodiment, the pulse generator is programmed to only respond to a transmission containing a pre-defined signal, such that the pulse generator and external wireless controller must first, and/or periodically "handshake" in order to communicate. Likewise, the pulse generator and/or controller may transmit encrypted signals which only can be decrypted by a key stored in the other of the pulse generator and/or controller. In another embodiment, RFID tagging technology may be used to ensure that the controller and pulse generator match. Any combination of these proximity and/or identity verification measures may be used to prevent cross-talk. Other useful technologies for ensuring security and identity in communication are, or may be available and are equally applicable.

FIG. 2A depicts schematically one embodiment of a garment electrode assembly 100. An inward-facing (toward the foot) surface of the electrode assembly 100 is shown. Electrode assembly may be a fabric or composite material, such as neoprene or latex and fabric material. The electrode assembly 100 has four wings 110 that wrap around a patient's foot. On each wing 110 is depicted a portion of a hook and loop fastener (e.g., Velcro®). Wings 110 on the left side of FIG. 2A have a hook portion 120 of a hook and loop fastener shown on the inward-facing surface of the assembly. Wings 110 on the right side of FIG. 2A have a loop portion 121 of a hook and loop fastener shown in phantom on the opposite, outward-facing surface of the assembly. Of course the placement of the hook and loop portions are a matter of design choice and one or both hook and loop pairs depicted may be reversed. Electrodes 131 and 132 for contacting a patient's foot are depicted on the inward-facing surface of the electrode assembly 100. Electric leads 134 and 135 are shown for connecting the electrodes 131 and 132 to a pulse generator. This embodiment would be useful where the electrodes are both placed on the plantar or dorsal side of the foot.

FIG. 2B depicts schematically a garment electrode assembly 200 that would be useful for stimulating across the foot, e.g., with one electrode on the dorsal side of the metatarsals of a patient and the other on the plantar side. A hook portion 220 of a hook and loop fastener is shown on the inward-facing surface of the assembly 200 on the left side of FIG. 2B. A hook portion 221 of a hook and loop fastener is shown in phantom on the outward-facing surface of the assembly 200 on the right side of FIG. 2B. Electrodes 231 and 232 for contacting a patient's foot are depicted on the inward-facing surface of the electrode assembly 100. Electric leads 234 and 235 are shown for connecting the electrodes 231 and 232 to a pulse generator.

Also provided herein is a method of stimulating a physiological response in a subject. The method comprises stimulating nerves of the foot of a patient using surface (skin) electrodes with electrical pulses at a frequency and amplitude able to either inhibit one or more of bladder contractions; rectum contractions; spongiosus and ischiocavernosus muscle contractions; urination; defecation; ejaculation; and pelvic pain of the bladder, urethra, prostate, anus or rectum, thereby obtaining the physiological response. The physiological response may be one or more of inhibition of micturition, defecation, ejaculation, bladder contractions, pelvic pain of bladder, urethra, prostate, anus, or rectum, and inhibition of rectal contractions. In one embodiment, the electrical pulses range from 1 Hz to 500 Hz, such as 1-50 Hz, 5-20 Hz, or 5 Hz. Voltage may range from 1-50V, such as from 1-20V or from 3-15V, which is suitable for inhibition of bladder contractions; rectum contractions; bulbospongiosus and ischiocavernosus muscle contractions; for inhibition or treatment of urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder, which are treatable by electrical stimulation. The pulses may be applied intermittently, for example and without limitation, in two or more stimulation intervals of, for example and without limitation, from 0.5 to 200 seconds with a rest period of no electrical stimulation able to inhibit bladder or rectal contractions between stimulation intervals. Typically during the rest period, no inhibitory stimulus is applied. During the rest period no electrical signal, or essentially no electrical signal is applied.

The following are non-limiting examples of the use of electrical stimulation of the foot to inhibit bladder contraction, and are exemplary only and are not intended to limit the scope of the inventions described herein in any way.

Example 1

Because previous studies have indicated that bladder activity could be modulated by somatic afferent input, in this study we explored the possibility that bladder overactivity could be suppressed by activation of afferent nerves in the foot or hand. This was tested in anesthetized cats by applying electrical stimulation through surface electrodes on the front or hind foot while monitoring reflex bladder activity. Stimulation of the foot or hand is non-invasive, easily accessible, and convenient, which could be a widely acceptable treatment for bladder overactivity if proven to be effective.

Methods:

1. Experimental Setup

Experiments were conducted in a total of 6 female cats (2.6 kg to 3.1 kg) under α-chloralose anesthesia (65 mg/kg, I.V. supplemented as necessary) after induction with isoflurane (2-3% in O2). Systemic blood pressure was monitored throughout the experiment via a catheter inserted in the right carotid artery. A tracheotomy was performed and a tube was inserted to keep the airway patent. A catheter for I.V. infusion was introduced into the right ulnar vein. The ureters were cut and drained externally. A double lumen catheter was inserted through the urethra into the bladder and secured by a ligature around the urethra. One lumen of the catheter was connected to a pump to infuse the bladder with either saline or 0.25% acetic acid (AA) at a rate of 0.5-2 ml/min, and the other lumen was connected to a pressure transducer to measure the pressure change in the bladder. After removal of the fur, surface self-adhesive pad electrodes (Grass F-E10ND, Astro-Med Inc., diameter: 1 cm) were attached to the skin area on the left hind foot (see FIG. 3). Similarly, electrodes were also attached to the left front foot for stimulation.

2. Stimulation Protocol

Figure 3:
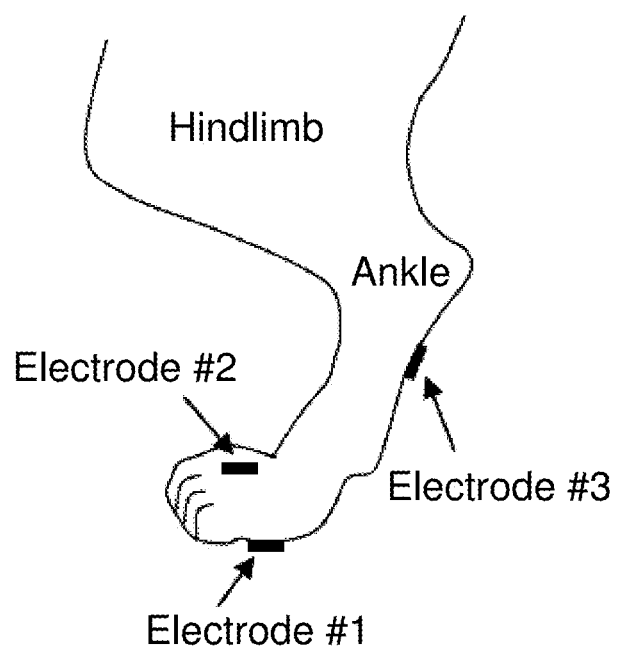
FIG. 3: Electrode placement for electrical stimulation of the cat hind foot.

Uniphasic rectangular pulses (0.2-1 ms pulse width) were delivered to the foot via the surface pad electrodes at a frequency of either 5 Hz or 20 Hz, based on our previous studies (Tai C, Smerin S E, de Groat W C, Roppolo J R. Pudendal-to-bladder reflex in chronic spinal cord injured cat. Exp Neurol 2006; 197:225-234 and Tai C, Shen B, Wang J, Chancellor M B, Roppolo J R, de Groat W C: Inhibitory and excitatory perigenital-to-bladder spinal reflexes in the cat. Am J Physiol Renal Physiol 2008; 294:F591-F602) that showed pudendal nerve stimulation inhibited bladder activity at 3-7 Hz, but excited bladder at 20 Hz. The threshold intensity to induce observable twitching of the toe was determined in each cat by a preliminary test at 5 Hz. Then, stimulation intensities at multiple thresholds of those to induce toe twitching were tested. Stimulation was applied via three combinations of electrodes as shown in FIG. 3 in order to find the effective electrode locations for bladder inhibition. Electrode 1 severed as the cathode in electrode combinations 1-2 and 1-3, but electrode 2 was the cathode when electrode combination 2-3 was used.

In the first group of experiments, the bladder was infused with saline to a volume about 100-110% of the bladder volume (i.e. bladder capacity) to induce large amplitude (>30 cmH2O), rhythmic reflex bladder contractions, and then maintained under isovolumetric conditions. At this bladder volume, foot stimulation at 5 and 20 Hz was applied to determine the effective frequency for bladder inhibition. The stimulation duration was always longer than the period of at least two bladder contractions to clearly demonstrate an inhibitory effect.

In the second group of experiments, the effect of 5 or 20 Hz stimulation was tested during a cystometrogram (CMG) which consisted of a slow infusion of saline (0.5-2 ml/min) starting with an empty bladder to determine the bladder capacity. Two or three CMGs were preformed without stimulation to obtain the control bladder capacity and evaluate reproducibility. Then, foot stimulation was applied during repeated CMGs. The inhibitory effect was evaluated by measuring the increase in bladder capacity during the stimulation. Stimulation and infusion were stopped after the onset of the first micturition reflex contraction which had a large amplitude (>30 cmH2O) and long duration (>30 sec). Control CMGs were also performed between periods of stimulation to examine if there was any persistent post-stimulation carry-over effect. The bladder was emptied after each CMG and a 5-10 min rest period was inserted between CMGs to allow the bladder reflex to recover. The two stimulation frequencies were tested in a randomized order in different animals.

In the third group of experiments, 0.25% AA was infused into the bladder to induce bladder irritation and overactivity. Then, experiments as described above were repeated in order to determine if the foot stimulation could also inhibit the irritation induced bladder overactivity.

3. Data Analysis

For the analysis of rhythmic bladder activity, the area under bladder pressure curve was measured during the stimulation and was normalized to the measurement during the same time period before the stimulation. For repeated CMG recordings using saline or AA infusion, the bladder capacities were measured and normalized to the measurement of the first control CMG during saline infusion. Repeated measurements in the same animal during the same experiment were averaged. The normalized data from different animals are presented as means±SE. One-sample Student's t-test and paired Student's t-test were used to detect statistical significance (P<0.05).

Results

1. Foot Stimulation During Saline Distension

Figure 4:
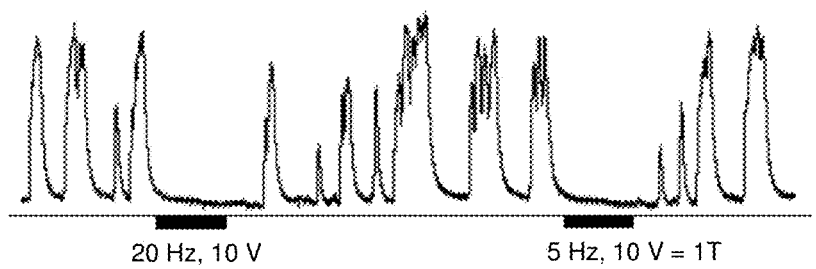
FIG. 4: Inhibition of isovolumetric bladder contractions by electrical stimulation applied to the hind foot via 3 different electrode configurations (A-C) as shown in FIG. 3. Stimulation of the front foot was not effective in inhibiting the bladder (D). The thin lines under the pressure traces indicate zero pressure. Black bars under the pressure traces indicate the stimulation duration. Stimulation pulse width was 1 ms. T=threshold to induce toe twitching. Data were from 4 different cats.
Figure 4:
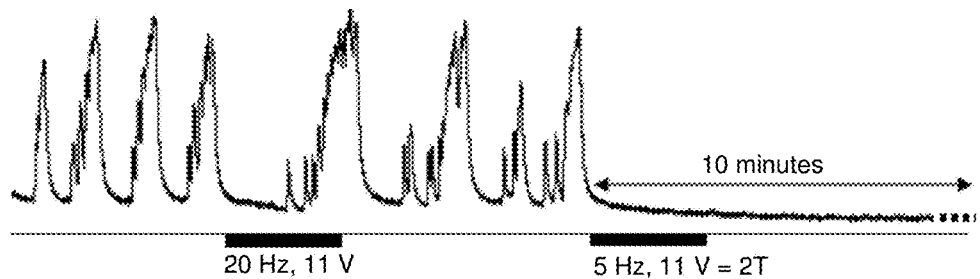
Figure 4:
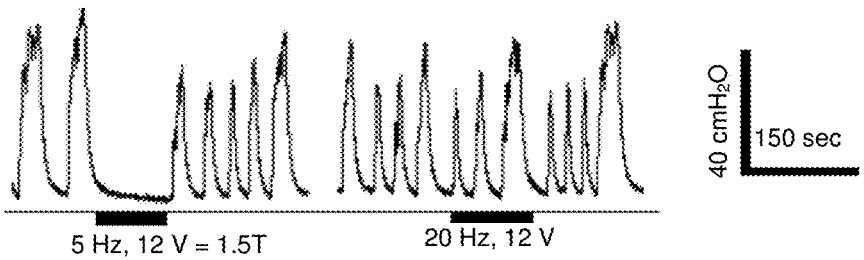
Figure 4:
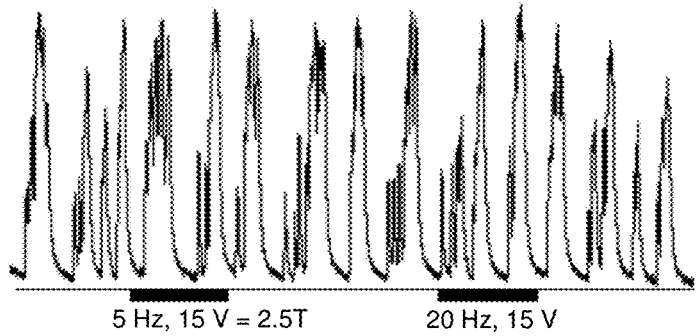

Under isovolumetric recording conditions with the bladder volume above the micturition volume threshold electrical stimulation of the hind foot inhibited reflex bladder activity (FIG. 4A-4C), but stimulation of the front foot failed to induce any inhibitory effect at various stimulation intensities (FIG. 4D, N=2 cats). Therefore, the remaining studies focused on hind foot stimulation which is termed foot stimulation in the following text and Figures.

Under isovolumetric conditions foot stimulation at both 5 Hz and 20 Hz inhibited the large amplitude, rhythmic bladder contractions with electrode combinations 1-2 (FIG. 4A, N=3 cats) and 1-3 (FIG. 4B, N=5 cats); whereas with electrode combination 2-3 which was tested in 1 cat, only 5 Hz stimulation was effective (FIG. 4C). Of particular note, 5 Hz stimulation also induced bladder inhibition lasting 5-10 minutes after the stimulation was terminated (FIG. 4B). This long-lasting effect was not observed with 20 Hz stimulation. These data are of particular importance indicating that long-lasting inhibitory effect can be obtained from short-term pulse durations. As described in Example 2, additional studies are ongoing that will examine and optimize the long-term effects from shorter-term stimulation.

Five Hz stimulation at intensities of 3-15 V which ranged from 0.5-2.5 times the threshold to induce toe twitching completely inhibited the isovolumetric bladder contractions (N=5 cats), while 20 Hz stimulation at intensities (5-15 V) ranging from 1-2.5 times threshold to induce toe twitching elicited a similar inhibition (90.8±9.1%, P<0.05) of the reflex contractions (N=5 cats). In 2 cats 5 Hz stimulation at an intensity as low as one half of the threshold to induce toe twitching was effective in completely inhibiting isovolumetric bladder contractions with electrodes 1-2 (FIG. 5A), but not with electrodes 1-3 (FIG. 5B). Lower stimulation intensities elicited partial inhibition consisting of either reduced amplitude bladder contractions (FIG. 5A at 0.25 T) or a significantly delayed large amplitude bladder contraction (FIG. 5B at 20 Hz).

Figure 6:
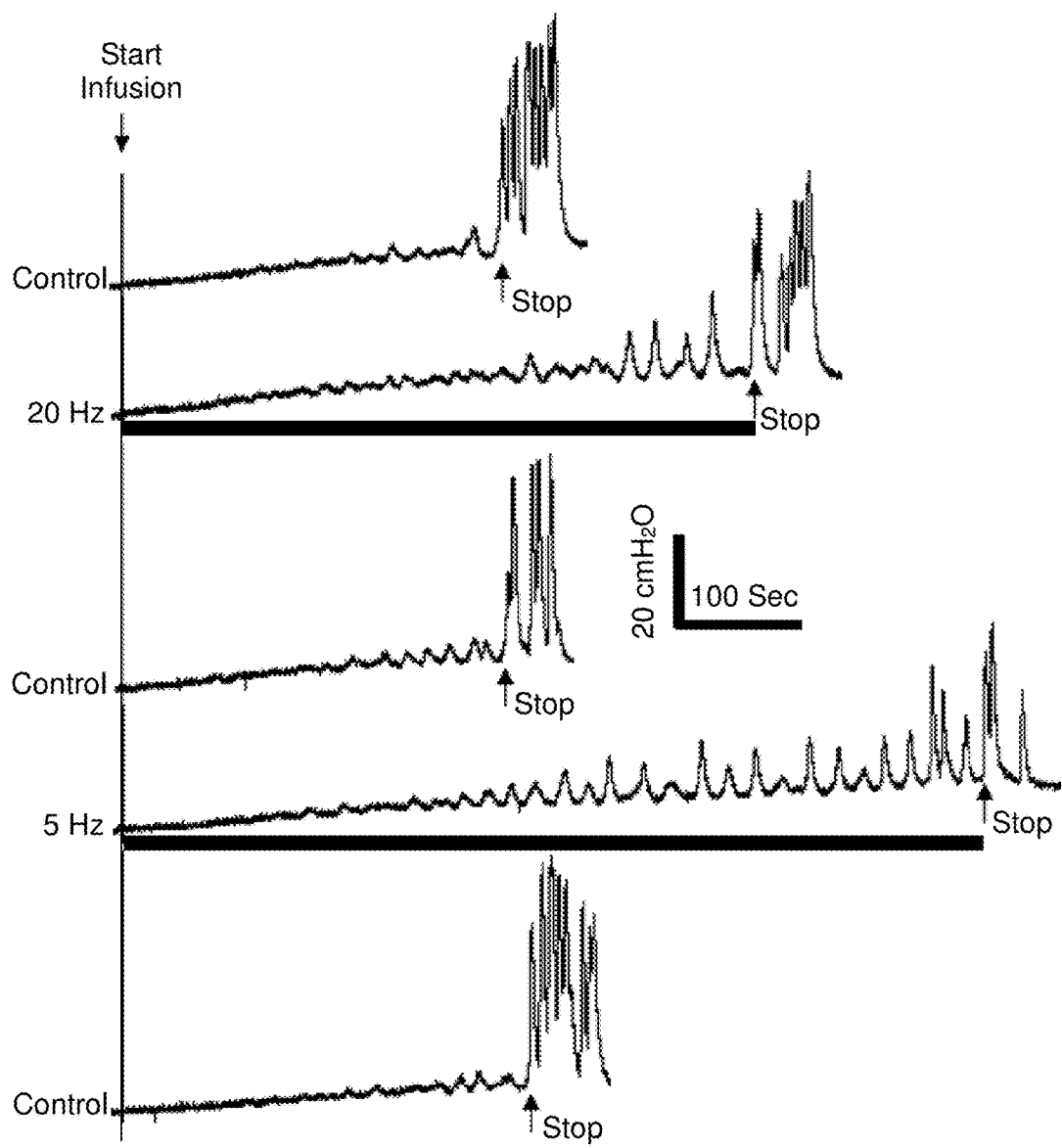
FIG. 6: Bladder capacity was increased by electrical stimulation of the foot at different frequencies (5 or 20 Hz). Stimulation intensity (12 V) was at 2 times of intensity threshold to induce toe movement. Stimulation pulse width was 1 ms. Electrodes 1-2 were used. The arrows indicate the start and stop of bladder infusion (2 ml/min). The black bars under the pressure traces indicate the stimulation duration.
Figure 7:
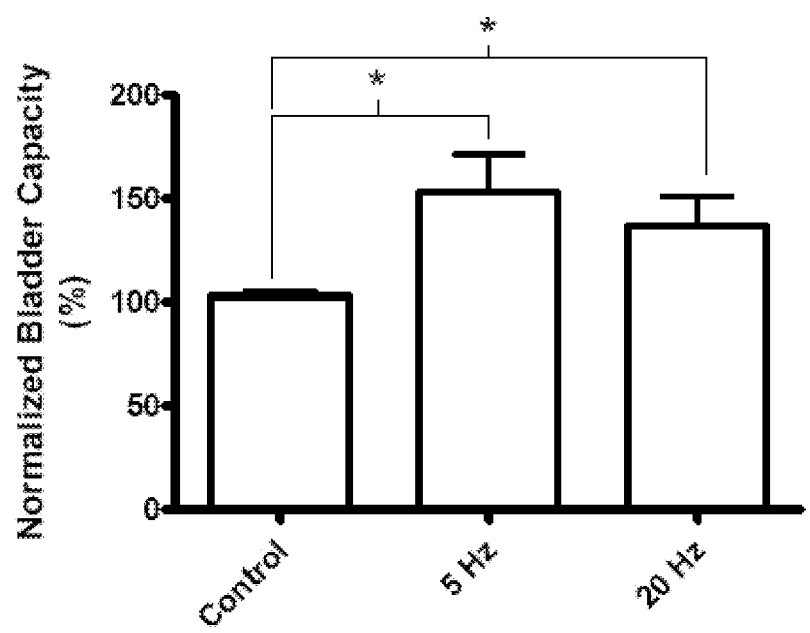
FIG. 7: Bladder capacity was significantly increased by electrical stimulation of the foot at different frequencies (5 or 20 Hz). Stimulation intensity (3-12 V) was at 1-2.5 times of intensity threshold to induce toe movement. Stimulation pulse width was 1 ms. Data were from total 5 cats. Electrodes 1-2 were used in 3 cats, and electrodes 1-3 were used in another 2 cats. * indicates statistical significance ($P<0.05$).

Foot stimulation at both 5 Hz and 20 Hz also significantly (P<0.05) increased bladder capacity to 153.2±18.2% and 136.9±14.3%, respectively, of the control bladder capacity (FIGS. 6 and 7). Stimulation intensities (3-12 V) about 1-2.5 times threshold to induce toe movement were effective (N=5 cats, 3 cats: electrodes 1-2; 2 cats: electrode 1-3). There was no significant difference between 5 Hz and 20 Hz effects. The inhibitory effect of foot stimulation was rapidly reversible within 5-10 minutes after termination of the stimulation and was repeatable at about 20 min intervals. Repeated foot stimulation during multiple CMG recordings did not elicit a post-stimulation effect on bladder capacity (FIG. 6).

2. Foot Stimulation During Acetic Acid (AA) Irritation

When the bladder was filled with 0.25% AA bladder capacity was significantly reduced (FIG. 8A) and large amplitude contractions were elicited at small bladder volumes (FIG. 7B). Foot stimulation at either 5 Hz or 20 Hz completely inhibited the large amplitude, isovolumetric bladder contractions induced by AA irritation (FIG. 8B, N=2 cats).

Figure 9:
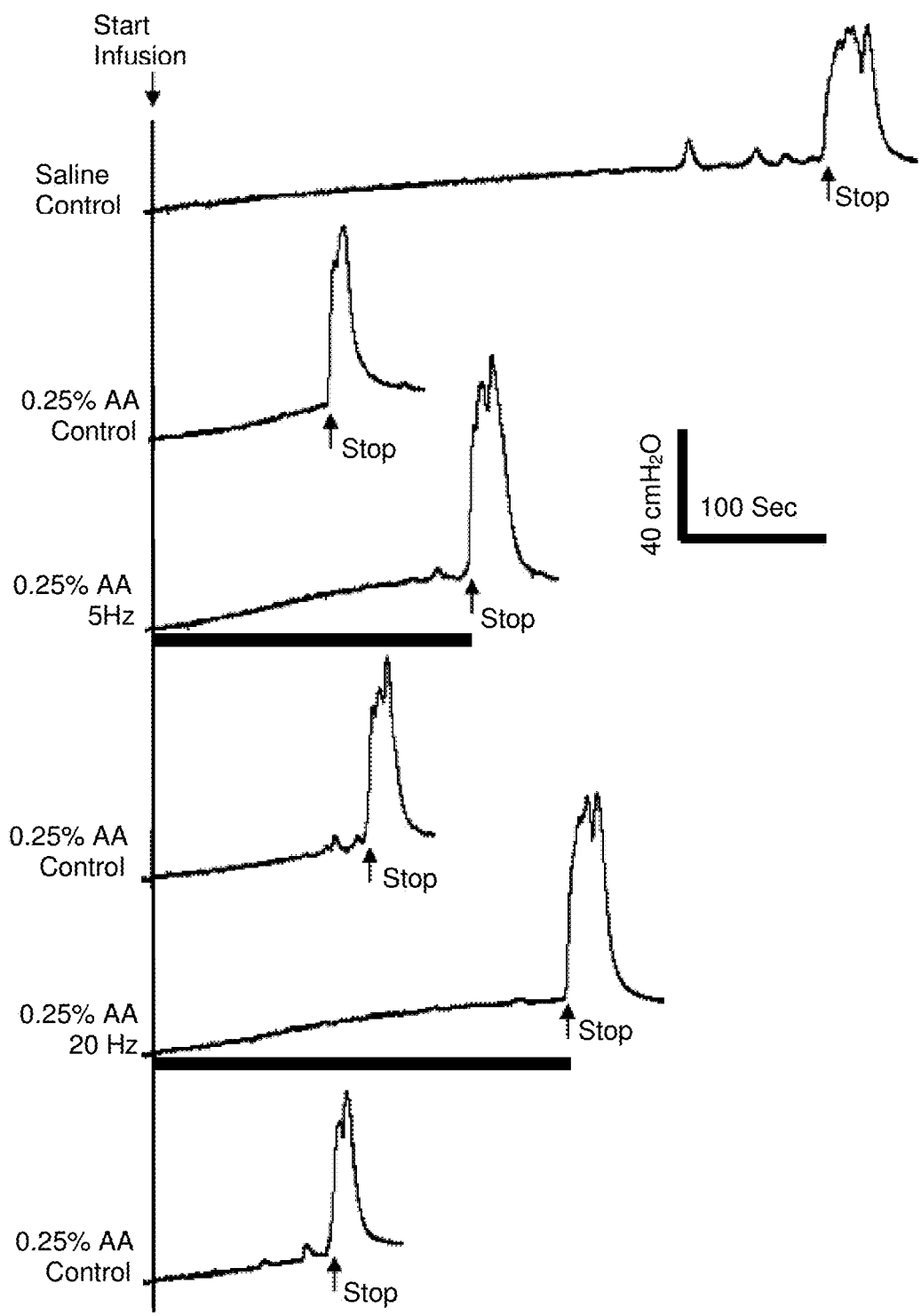
FIG. 9: Reduction in bladder capacity induced by 0.25% acetic acid (AA) was partially reversed by foot stimulation at different frequencies (5 or 20 Hz). Stimulation intensity (10 V) was at 1.25 times of intensity threshold to induce toe movement. Stimulation pulse width was 1 ms. Electrodes 1-2 were used. The arrows indicate the start and stop of bladder infusion (2 ml/min). The black bars under the pressure traces indicate the stimulation duration.
Figure 10:
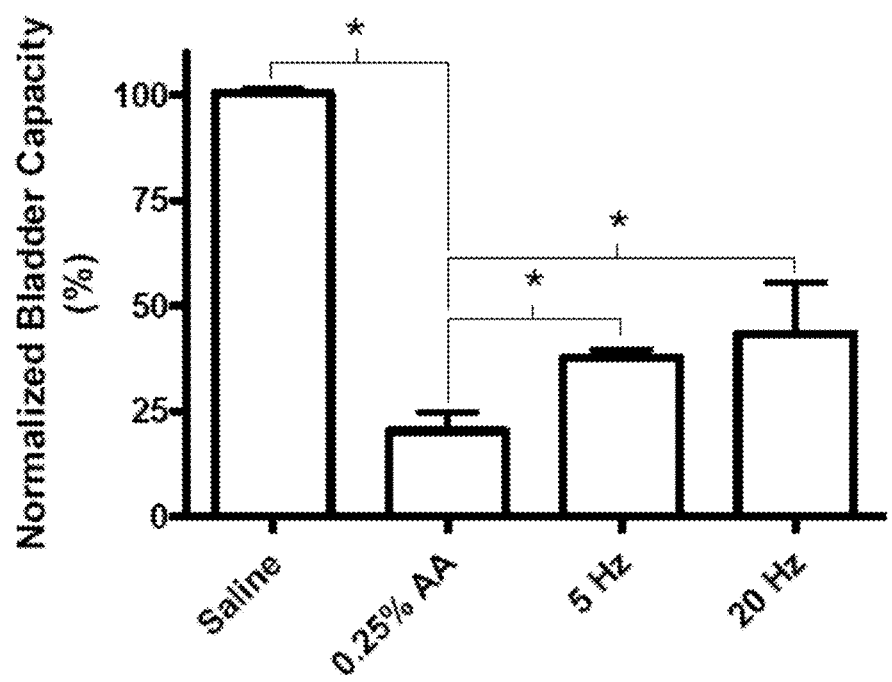
FIG. 10: Reduction in bladder capacity induced by 0.25% acetic acid (AA) was partially reversed by foot stimulation at different frequencies (5 or 20 Hz). Stimulation intensity (6-12 V) was at 1.25-3 times of intensity threshold to induce toe movement. Stimulation pulse width was 1 ms. Electrodes 1-2 were used in total 4 cats. * indicates statistical significance ($P<0.05$).

AA irritation significantly (P<0.05) reduced bladder capacity to 20.3±8.9% of the control bladder capacity measured during saline infusion (FIGS. 9 and 10). Foot stimulation partially reversed the effect of AA irritation, increasing the bladder capacity to 37.6±2.1% and 43.5±12.0% of the saline control bladder capacity at frequencies of 5 Hz and 20 Hz, respectively (FIGS. 9 and 10). There was no significant difference between 5 Hz and 20 Hz effects.

Discussion

This study showed that electrical stimulation of the foot was effective in inhibiting reflex bladder activity and increasing bladder capacity in anesthetized cats. Although 5 Hz stimulation was superior to 20 Hz in some cases (FIGS. 4B-C and FIGS. 5-7), there was on average no significant difference between these two frequencies in inhibiting reflex bladder activity (FIGS. 7 and 10). These results provided urodynamic evidence indicating that electrical stimulation of the foot might be an effective treatment for bladder overactivity.

All three electrode combinations (FIG. 3) are effective in inhibiting bladder activity (FIG. 4), indicating that afferent activation of a specific nerve in the foot might not be required. There are two major nerves innervating the foot. Branches from the peroneal nerve run on the dorsal (top of the foot, as is understood in the medical arts) surface of the foot, while the tibial nerve mainly branches on the plantar (bottom/sole of the foot, as is understood in the medical arts) surface of the foot. Electrical stimulation used in this study probably activated nerve branches from both peroneal and tibial nerves, indicating that specifically targeting the posterior tibial nerve as currently used in clinical settings might not be necessary. Previous studies in both cat (Wang J, Liu H, Shen B, Roppolo J R, de Groat W C, Tai C: Bladder inhibition or excitation by electrical perianal stimulation in a cat model of chronic spinal cord injury. BJU Int 2009; 103:530-536) and monkey (Sato A, Sato Y, Schmidt R. Reflex bladder activity induced by electrical stimulation of hind limb somatic afferents in the cat. J Auto Nerv Sys 1980; 1:229-241) have shown that electrical stimulation of the peroneal nerve in the hindlimb also inhibits reflex bladder activity.

Figure 5:
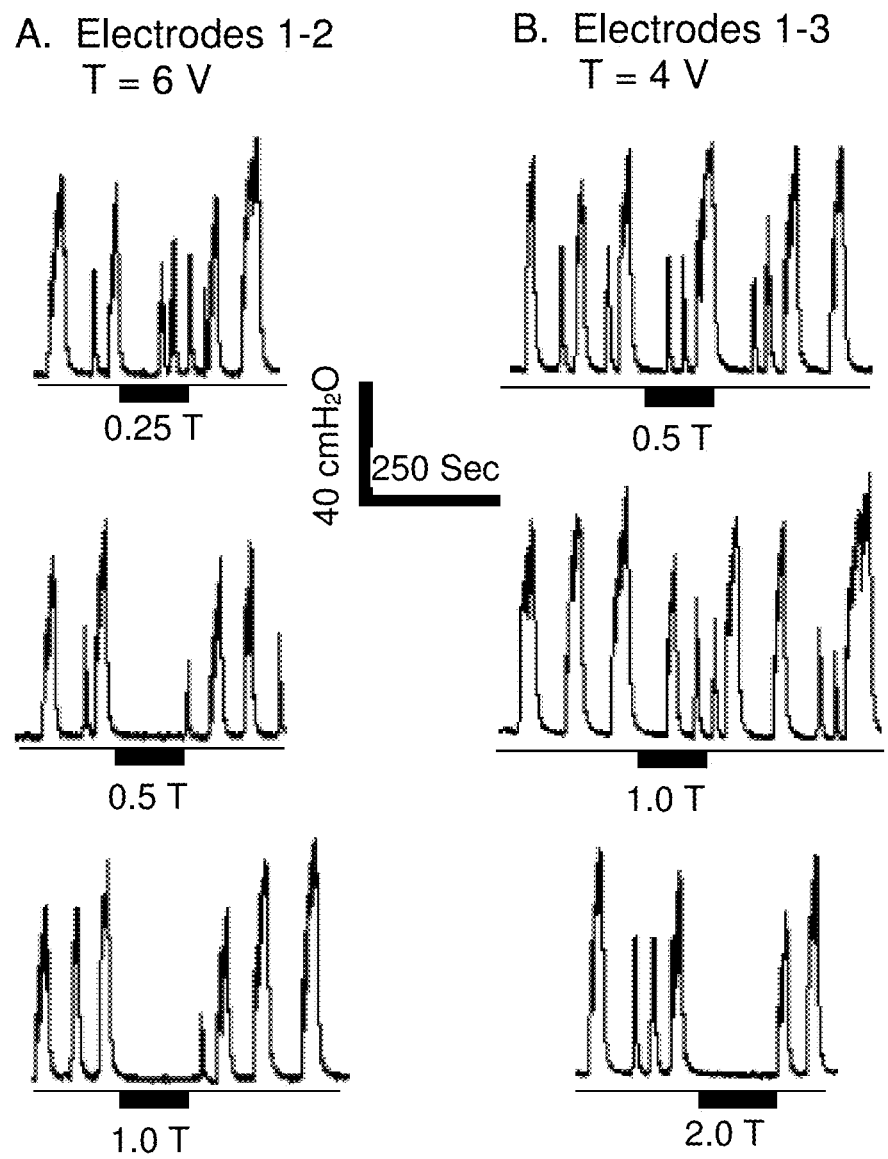
FIG. 5: Inhibition of isovolumetric bladder contractions by 5 Hz electrical stimulation of the foot. A. Complete inhibition was achieved at one half of the intensity threshold (T=6 V) for inducing toe movement with electrodes 1-2. B. Complete inhibition was achieved at 2 times of the intensity threshold (T=4 V) for inducing toe movement with electrodes 1-3. The thin lines under the pressure traces indicate zero pressure. Black bars under the pressure traces indicate the stimulation duration. Stimulation pulse width was 1 ms. Data in A and B were from the same animal.

An advantage of foot stimulation is that the nerves in the foot are much closer to the skin surface than peroneal or posterior tibial nerve which is located deeper between the leg muscles. Therefore, electrical activation of the nerves on the foot requires only surface electrodes and is much easier than the posterior tibial nerve stimulation that is usually performed by inserting a needle electrode close to the nerve. However, it is worth noting that foot stimulation did not induce a long-lasting inhibitory effect during repeated CMG tests on the same day (FIG. 5). This is different from the clinical reports of posterior tibial nerve stimulation applied over the course of many weeks where the inhibitory effect could last weeks or months. This difference might occur due to different species, presence of anesthesia, or different stimulation parameters, as well as different stimulation locations. As indicated in FIG. 4B, certain stimulation parameters produced post-stimulation effects. Ongoing studies are planned to determine optimal stimulation conditions for doing so. Nevertheless, that stimulation is non-invasive means a patient can stimulate their foot at any time for any duration, and even discreetly. As such stimulation resulting in inhibition periods of more than hours or days are not as necessary as in the case where a patient needs invasive outpatient procedures to achieve the same results. As shown in FIG. 5A, the inhibitory effect may be achieved at an intensity below the threshold to induce toe movement.

Electrical stimulation of the front foot in this study failed to induce an inhibitory effect on reflex bladder activity, while stimulation of the hind foot was effective. This suggests that the spinal segmental distribution of the stimulated somatic afferent pathways is an important factor in the efficacy of this type of neuromodulation. In the cat, the afferent projections from the hind foot into the spinal cord exhibit some segmental overlap in the lumbosacral spinal cord with the afferent projections from the lower urinary tract (LUT), providing a greater possibility of spinal interactions between hind foot and LUT afferent pathways. Therefore, it is probable that the somatic afferent input from the hind foot inhibits the micturition reflex at the sacral spinal cord level. However, inhibition at a supraspinal site cannot be excluded. A previous study in cats (McPherson A. The effects of somatic stimuli on the bladder in the cat. J Physiol 1966; 185: 185-196) showed that the inhibitory effect on bladder activity elicited by electrical stimulation of the nerves from hindlimb muscles was lost after chronic spinal cord transaction at the thoracic level, indicating a possible role of the supraspinal mechanisms in somato-vesical inhibition. The same study also showed that activation of large myelinated afferent nerves (conduction velocity about 50 m/s) induced the inhibition. Our experiments which showed that foot stimulation produced inhibition at stimulation intensities 1-2 times threshold support this conclusion. However another study (Sato A, Sato Y, Schmidt R. Reflex bladder activity induced by electrical stimulation of hind limb somatic afferents in the cat. J Auto Nerv Sys 1980; 1:229-241) identified a role of small myelinated or unmyelinated hind limb afferent nerves in somato-vesical inhibition in the cat.

Recent studies in the cats (Tai C, Smerin S E, de Groat W C, Roppolo J R. Pudendal-to-bladder reflex in chronic spinal cord injured cat. Exp Neurol 2006; 197:225-234; Tai C, Shen B, Wang J, Chancellor M B, Roppolo J R, de Groat W C: Inhibitory and excitatory perigenital-to-bladder spinal reflexes in the cat. Am J Physiol Renal Physiol 2008; 294:F591-F602; and Wang J, Liu H, Shen B, Roppolo J R, de Groat W C, Tai C: Bladder inhibition or excitation by electrical perianal stimulation in a cat model of chronic spinal cord injury. BJU Int 2009; 103:530-536) showed that the effect of pudendal nerve stimulation on bladder activity was dependent on the stimulation frequency. At 3-7 Hz, pudendal nerve stimulation significantly inhibited the bladder, but at 20-40 Hz it could excite the bladder. However, this frequency dependency was not observed in this study. Foot stimulation significantly inhibited the bladder at both 5 Hz and 20 Hz (FIGS. 4-10), indicating that the underlying mechanisms of bladder modulation by foot stimulation and pudendal nerve stimulation might be different, even though in our cat model they appear to be equally effective in suppressing reflex bladder activity (Tai C, et al. Exp Neurol 2006; 197:225-234 and Tai C, et al. Am J Physiol Renal Physiol 2008; 294:F591-F602). This similar inhibitory efficacy in cats of foot stimulation and pudendal nerve stimulation which has also been shown clinically to be effective in treating bladder overactivity (Peters K M, Feber K M, Bennett R C: Sacral versus pudendal nerve stimulation for voiding dysfunction: a prospective, single-blinded, randomized, crossover trial. Neurourol Urodyn 2005; 24:643-647 and Peters K M, Feber K M, Bennett R C: A prospective, single-blind, randomized crossover trial of sacral vs pudendal nerve stimulation for interstitial cystitis. BJU Int 2007; 100:835-839) suggests that foot stimulation might also be a useful treatment for bladder overactivity in humans.

Figure 8:
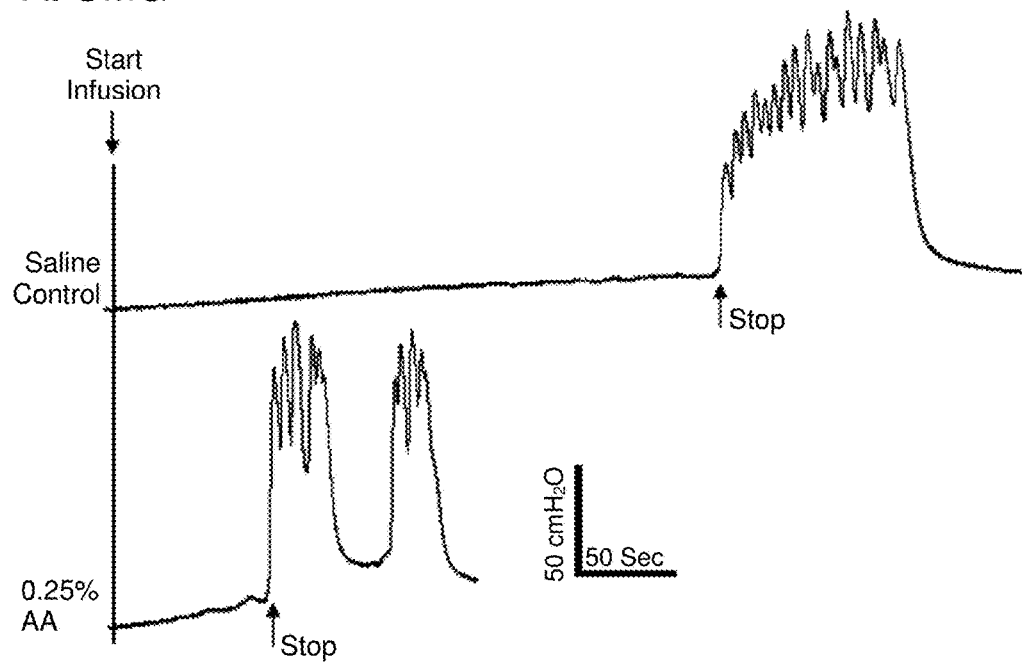
FIG. 8: Foot stimulation inhibited bladder overactivity induced by 0.25% acetic acid (AA). A. 0.25% AA irritated bladder, caused bladder overactivity, and reduced bladder capacity during CMG. The arrows indicate the start and stop of the infusion (2 ml/min). B. The overactive bladder contractions under isovolumetric condition at a smaller bladder volume as shown in A was inhibited by foot stimulation. The thin lines under the pressure traces indicate zero pressure. Black bars under the pressure traces indicate the stimulation duration. Stimulation pulse width was 0.2 ms. Electrodes 1-2 were used.
Figure 8:
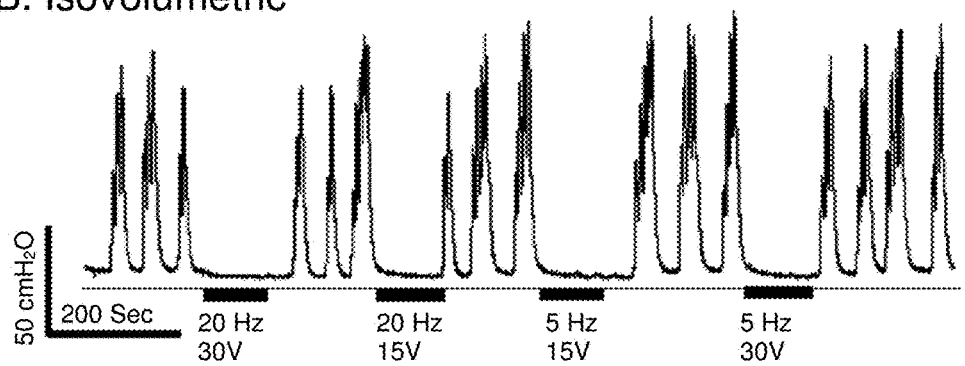

Foot stimulation inhibited not only the bladder activity induced by saline distention (FIGS. 4-7), but also the bladder overactivity induced by AA irritation (FIGS. 8-10). However, the marked reduction in bladder capacity (80%) caused by AA irritation was only partially reversed by foot stimulation to about 40-50% of the saline control bladder capacity (FIGS. 9 and 10). The ability of foot stimulation to inhibit bladder overactivity induced by AA irritation is clinically relevant, because AA irritation activates the C-fiber afferents that play an important role in the generation of bladder overactivity under pathological conditions. Pudendal nerve stimulation produced similar inhibitory effects in the AA model in cats (Shen B, et al. Bladder activity modulated by transcutaneous pudendal nerve stimulation. 2008 Neuroscience Meeting Abstract. Washington D.C.: Society for Neuroscience, 2008).

Further animal studies are needed to explore a broader range of stimulus patterns and frequencies as well as different electrode placements on the foot stimulation to determine if efficacy can be improved particularly in regard to suppressing bladder overactivity induced by AA. Only continuous stimulation was used in this study, which might not be the optimal stimulus to induce and maintain the inhibitory effect. Intermittent stimulation with on and off periods might further enhance the inhibitory effect. Furthermore, different electrode placements which increase the probability of activating either cutaneous or muscle afferents should be tested to determine if one type of afferent pathway is more effective in controlling bladder activity.

This study demonstrated the potential of a non-invasive electrical stimulation method using electrodes applied to skin of the foot to inhibit bladder over activity. Toe movement and sensory responses might be a side effect of the treatment, but would be justified by the benefits of suppressing bladder dysfunction. In summary, the present study indicates that a non-invasive, convenient method to treat overactive bladder symptoms, and as a result methods of treatment of urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder, could be developed utilizing transcutaneous stimulation of somatic nerves in the foot.

Example 2

Experiments are conducted in cats to determine the duration of post-stimulation inhibition of bladder contractions. Animals are prepared essentially as described in Example 1. Experiments are conducted in female cats (2.6 kg to 3.1 kg) under α-chloralose anesthesia (65 mg/kg, I.V. supplemented as necessary) after induction with isoflurane (2-3% in O2). Systemic blood pressure is monitored throughout the experiment via a catheter inserted in the right carotid artery. A tracheotomy is performed and a tube is inserted to keep the airway patent. A catheter for I.V. infusion is introduced into the right ulnar vein. The ureters were cut and drained externally. A double lumen catheter was inserted through the urethra into the bladder and secured by a ligature around the urethra. One lumen of the catheter was connected to a pump to infuse the bladder with either saline or 0.25% acetic acid (AA) at a rate of 0.5-2 ml/min, and the other lumen was connected to a pressure transducer to measure the pressure change in the bladder. After removal of the fur, surface self-adhesive pad electrodes (Grass F-E10ND, Astro-Med Inc., diameter: 1 cm) are attached to the skin area on the hind foot essentially as shown in FIG. 3.

Stimulation Protocol

Uniphasic rectangular pulses (0.2-1.0 ms pulse width) at low (5 Hz), medium (20 Hz) or high (30 Hz) frequency are delivered to the electrode pairs. The intensity threshold for inducing toe movement is determined by gradually increasing the stimulation intensity (voltage). Then, multiples of the threshold intensity are used for foot stimulation.

In the first group of experiments, the bladder is infused with saline to a volume about 100-110% of the threshold volume (i.e. bladder capacity) for inducing large amplitude (>30 cmH2O), rhythmic reflex bladder contractions, and is then maintained under isovolumetric conditions. At this bladder volume, the foot is stimulated at different frequencies (5 Hz, 20 Hz or 30 Hz) to determine the effective frequencies for inhibiting bladder activity. The stimulation duration (3-5 minutes) is always longer than the period of at least two bladder contractions in order to clearly demonstrate an inhibitory effect. In order to determine if the stimulation increased bladder capacity, several cystometrograms (CMGs) are performed before and after the recording of rhythmic isovolumetric bladder contractions during which short duration nerve stimulation is applied multiple times. The CMGs consists of a slow infusion of saline (0.5-2 ml/min) starting with an empty bladder.

In the second group of experiments, the post-stimulation effect of prolonged (30 minute) foot stimulation is examined by performing repeated CMGs. Initially two or three CMGs are preformed without stimulation to obtain the control bladder capacity and evaluate reproducibility. Then, two groups of experiments are conducted: 1) Control group without stimulation and 2) Treatment group with foot stimulation (further broken down into groups for different electrode combinations, 1-2, 1-3 and/or 2-3 as described in Example 1. In the treatment group the bladder volume is maintained at a volume slightly above the bladder capacity to induce rhythmic isovolumetric bladder contractions. Then, foot stimulation (frequency: 5, 20 or 30 Hz; intensity: 2-4 times threshold for inducing toe movement) is applied for 30 minutes to inhibit the isovolumetric contractions. After the 30 minute stimulation, 5 CMGs are performed within a 1.5-2 hour period to examine the change of bladder capacity. At the end of the fifth CMG, the bladder volume is again maintained at a volume slightly above the bladder capacity to induce rhythmic isovolumetric contractions, during which a second 30 minute foot stimulation is applied to inhibit the contractions. The post-stimulation effect on bladder capacity induced by the second 30 minute stimulation is evaluated by another 5 CMGs repeated within 1.5-2 hours after the termination of the second stimulation treatment. The stimulation frequency (5, 20 or 30 Hz) was randomized between the first and second 30 minute treatment. In the control group the procedures similar to those used in the treatment group are performed, but the foot stimulation is not applied during either the first or the second 30 minute treatment period. Instead, the rhythmic isovolumetric bladder contractions are allowed to continue during each 30 minute period. The bladder is emptied after each CMG and a 5-10 min rest period is inserted between CMGs to allow the distended detrusor to recover. The 30 minute stimulation duration is chosen to mimic the clinical application of 30 minute foot stimulation. At the end of the second group of experiments after examining the post-stimulation effect of nerve stimulation, the foot stimulation is applied again during the CMGs to determine if the bladder capacity could be further increased.

Animals used in the first group of experiments, in which repeated short periods of nerve stimulation are applied during rhythmic isovolumetric bladder contractions, also receive 30 minute stimulation treatments later in the experiments in order to compare the effects with those elicited in the second group of experiments where short periods of stimulation are not applied before the 30 minute stimulation.

Data Analysis

For the analysis of rhythmic isovolumetric bladder contractions, the area under bladder pressure curve is measured during foot nerve stimulation and is normalized to the measurement during the same time period before the stimulation. For the repeated CMG recordings, the bladder capacities are measured and normalized to the measurement of the first control CMG in each experimental group. Repeated measurements in the same animal during the same experiment are averaged. The normalized data from different animals are presented as means±SE. ANOVA followed by Bonferroni post-tests and Student's t-test are used to detect statistical significance ($P<0.05$).

Results (Expected)—Foot nerve stimulation inhibits rhythmic isovolumetric reflex bladder contractions; prolonged foot stimulation elicits a persistent post-stimulation increase in bladder capacity; and foot stimulation during CMGs further increases bladder capacity.

Example 3

Inhibition of bladder contraction in a human patient is tested by placing electrodes in one or more of three positions on the foot of one or more human patients. The three positions include: 1) two electrodes attached on the bottom of the foot, between the metatarsals and calcaneus bones; 2) two electrodes attached on top of the foot: between the talus/navicular and metatarsal bones; and 3) two electrodes attached one on top and another on the bottom of the foot: across the metatarsal bones.

Patients are divided into at least two groups, one group receiving electrical stimulus and one group not receiving electrical stimulus. Patients are to drink a liquid, e.g., water, until bladder urgency (an urge to urinate) is felt, at which time biphasic electrical stimulus is applied with a pulse frequency of between 1-50 Hz, pulse lengths of between 0.1 and 3 ms, and a voltage of between 1 and 50V. Urge to urinate is tested at regular intervals prior to, during and after electrical stimulation, and at the same regular intervals for non-stimulated patients. The urge to urinate is a subjective scale ranging from no urge to urinate and extreme urgency, requiring immediate voiding (e.g., a scale of 1 to 10 with "1" being no urge to urinate and "10" being extreme urgency. Depending on the electrical stimulus parameters, patients receiving electrical stimulus in the ranges tested are expected to experience reduced urgency during electrical stimulation, and, in many cases after electrical stimulation. The patient population for this study also may include or be limited to patients with: urological conditions, such as overactive bladder (OAB) symptoms including bladder overactivity, urinary frequency, urinary urgency, urinary incontinence, interstitial cystitis (IC), urinary retention, and pelvic pain; gastrointestinal conditions, such as fecal incontinence, irritable bowel syndrome (IBS), and constipation; and sexual conditions, such as premature ejaculation, erectile disorder, and female sexual arousal disorder, with appropriate non-stimulated control subjects.

Another experiment could use the patient's urinary diary to record the frequency, urgency, number of incontinence, etc. before, during and after foot stimulation treatment.

Yet another experiment could use urodynamic test (e.g., cyctometrogram) to record bladder activity (e.g., detrusor overactivity, bladder capacity, first desire to void, micturition pressure and duration, etc.) before, during, and after foot stimulation treatment.

Having described this invention, it will be understood to those of ordinary skill in the art that the same can be performed within a wide and equivalent range of conditions, formulations and other parameters without affecting the scope of the invention or any embodiment thereof. All references cited herein are incorporated herein by reference in their entirety for their technical disclosure.

What is claimed is:

1. A method of treating fecal incontinence in a patient, comprising:

transcutaneously delivering pulsed electrical energy directly to a foot of the patient through a device comprising a plurality of electrodes placed on the skin of the patient's foot, the pulsed electrical energy comprising electrical pulses having a frequency ranging from 1 Hz to 500 Hz and a voltage ranging from 1 V to 50 V, the electrical pulses configured to inhibit rectal contractions in the patient, wherein the electrodes are arranged such that:

two or more electrodes are in contact with the skin on a dorsal surface of the patient's foot, and at least two of the electrodes have opposite polarities;

two or more electrodes are in contact with the skin on a plantar surface of the patient's foot, and at least two of the electrodes have opposite polarities; or at least one electrode is in contact with the skin on the dorsal surface of the patient's foot and at least one electrode is in contact with the skin on the plantar surface of the patient's foot, and at least one electrode in contact with the skin on the dorsal surface of the patient's foot has an opposite polarity from at least one electrode in contact with the skin on the plantar surface of the patient's foot.

2. The method of claim 1, wherein the electrical pulses are applied by one or more surface electrodes on skin of the dorsal side of the foot about one or more metatarsal bones and one or more surface electrodes of opposite polarity on skin of the plantar side of the foot about one or more metatarsal bones.

3. The method of claim 1, wherein the electrical pulses are applied by one or more surface electrodes on skin of the dorsal side of the foot about one or more metatarsal bones and one or more surface electrodes of opposite polarity on skin of the dorsal side of the foot about one or more of the talus, cuboid, intermediate cuneiform, lateral cuneiform or navicular bones.

4. The method of claim 1, wherein the electrical pulses are applied by one or more surface electrodes on skin of the plantar side of the foot about one or more metatarsal bones and one or more surface electrodes of opposite polarity on skin of the plantar side of the foot about the calcaneous bone.

5. The method of claim 1, in which the pulses are biphasic.

6. The method of claim 5, in which the pulses are symmetrical, square, or rectangular.

7. The method of claim 5, in which the pulses are charge balanced.

8. The method of claim 1, wherein the pulses are applied in two or more stimulation intervals of from 0.5 to 200 seconds with a rest period of no electrical stimulation able to inhibit rectal contractions between stimulation intervals.

9. The method of claim 1, in which the pulses are applied at a voltage less than an intensity threshold to induce toe movement (T) in a patient.

10. The method of claim 1, in which the electrical pulses are applied by electrodes in a garment electrode.

11. The method of claim 1, in which the pulse frequency ranges from 1 Hz to 50 Hz.

12. The method of claim 1, in which the pulse frequency ranges from 5 Hz to 20 Hz.

13. The method of claim 1, in which the pulse frequency is approximately 5 Hz.

14. The method of claim 1, in which the voltage ranges from 3V to 12V.

15. The method of claim 1, in which the voltage ranges from 0.5 T to 4 T, where T is a toe-twitch threshold of the patient.

16. The method of claim 1, in which the duration of pulses ranges from 0.1 ms to 3 ms or from 0.2 ms to 1 ms.

17. The method of claim 1, in which the duration of pulses is approximately 1 ms.

18. The method of claim 1, wherein the electrical pulses have a frequency of about 20 Hz.

19. The method of claim 1, wherein the fecal incontinence is associated with irritable bowel syndrome or an inflammatory bowel disease in a patient.

20. A method of treating fecal incontinence in a patient, comprising:

transcutaneously delivering pulsed electrical energy directly to a foot of the patient through a device, the device comprising:

an electrode assembly comprising a plurality of inward facing electrodes, the assembly configured such that one or more of the electrodes contacts the skin of the patient on a plantar surface of the patient's foot and/or one or more of the electrodes contacts the skin of the patient on the dorsal surface of the patient's foot, wherein at least one of the electrodes has a first polarity and another of the electrodes has an opposite polarity, wherein the pulsed electrical energy comprises electrical pulses having a frequency ranging from 1 Hz to 500 Hz and a voltage ranging from 1 V to 50 V, the electrical pulses are configured to inhibit rectal contractions in the patient.

* * * * *

UNITED STATES PATENT AND TRADEMARK OFFICE
CERTIFICATE OF CORRECTION

PATENT NO.       : 10,315,029 B2
APPLICATION NO.  : 15/848143
DATED            : June 11, 2019
INVENTOR(S)      : Changfeng Tai Page 1 of 1

It is certified that error appears in the above-identified patent and that said Letters Patent is hereby corrected as shown below:

In the Claims

Column 21, Line 42, Claim 4, delete "calcaneous" and insert -- calcaneus --

Signed and Sealed this
Tenth Day of September, 2019

Andrei Iancu
*Director of the United States Patent and Trademark Office*